United States Patent [19]

Stanly et al.

[11] 3,991,747

[45] Nov. 16, 1976

[54] PORTABLE CARDIAC MONITORING SYSTEM AND METHOD

[75] Inventors: Albert L. Stanly, Los Angeles; Gunther W. Wimmer, Saugus, both of Calif.

[73] Assignee: Albert L. Stanly, Los Angeles, Calif.

[22] Filed: Aug. 5, 1974

[21] Appl. No.: 495,091

Related U.S. Application Data

[63] Continuation of Ser. No. 265,473, June 23, 1972, abandoned.

[52] U.S. Cl. .................. 128/2.06 R; 128/2.06 B; 128/2.06 E; 128/2.1 A; 128/419 PT
[51] Int. Cl.² .......................................... A61B 5/04
[58] Field of Search ........ 128/206 A, 206 B, 206 C, 128/206 E, 206 G, 206 R, 206 V, 2.1 A, 419 P, 419 PT

[56] References Cited
UNITED STATES PATENTS

| | | | |
|---|---|---|---|
| 2,400,583 | 5/1946 | White | 128/2.06 B |
| 2,571,223 | 10/1951 | Edinburg | 128/2.06 B |
| 2,865,366 | 12/1958 | Partridge | 12/2.06 B |
| 3,565,058 | 2/1971 | Mansfield | 128/2.06 R |
| 3,620,208 | 11/1971 | Higley et al. | 128/2.06 E |
| 3,757,778 | 9/1973 | Graham | 128/2.06 R |

OTHER PUBLICATIONS
Fontenier, "Medical & Biological Engineering", vol. 10, No. 2, Mar. 1972, pp. 175–178.

*Primary Examiner*—William E. Kamm
*Attorney, Agent, or Firm*—Fraser and Bogucki

[57] ABSTRACT

A plurality of electrodes affixed at selected positions of the chest of an ambulatory patient sense potentials due to cardiac or pacemaker action of the patient, for transmission by radio, telephone or other means to an EKG and pacemaker performance measuring and analyzing facility. The electrodes are connected to timing, control and signal processing means contained in a smal, conveniently worn or stored housing. Signals from sequenced, selected combinations of electrodes are serially transmitted for given intervals after modification, and in the case of telephone transmission are converted to audio output. The pairs of electrodes are arrayed to yield substantially all the data, from as few as four electrodes connected to provide bipolar leads, obtainable from the conventional 12 lead EKG. The signal processing system includes highly sensitive stable circuit elements providing low current, very high impedance operation and minimizing variations and limitations imposed by electrode attachment, as well as minimizing local variation in skin resistance of the patient and common mode operation with conventional electrical sources. Means are provided for processing and transmitting a power source signal as a marker and as an indication of the effectiveness and remaining useful life of the power source which may comprise an ordinary falshlight battery. Where a pacemaker is used, the transmitted signals are in a form to provide data for evaluation of the pacemaker effectiveness. At the receiving end, the transmitted signals are recorded or displayed on an EKG recorder, tape recorder, oscilloscope, or heart-pacer condition readout apparatus.

29 Claims, 13 Drawing Figures

FIG.−1
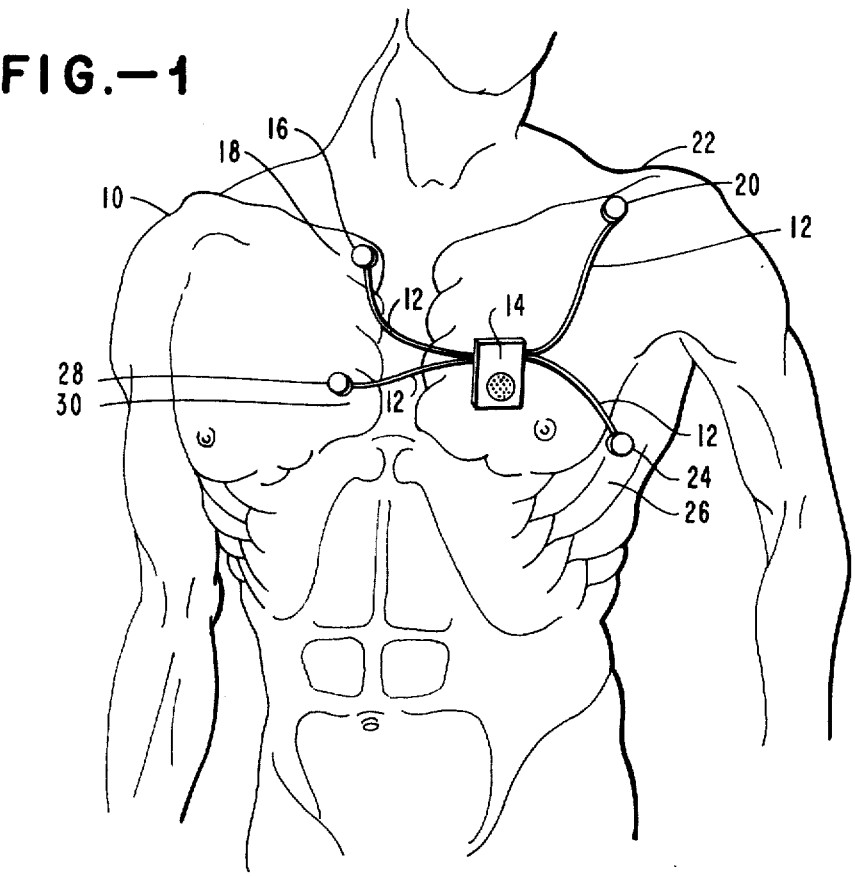
FIG.−2A
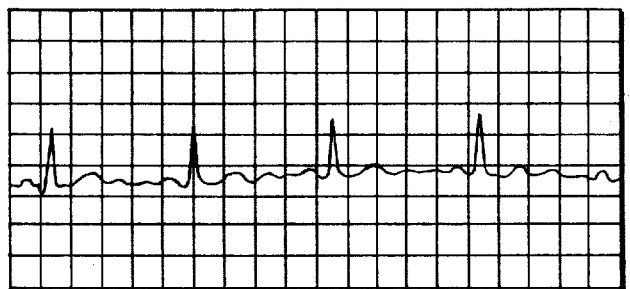
STANDARD LEAD I
FIG.−2B
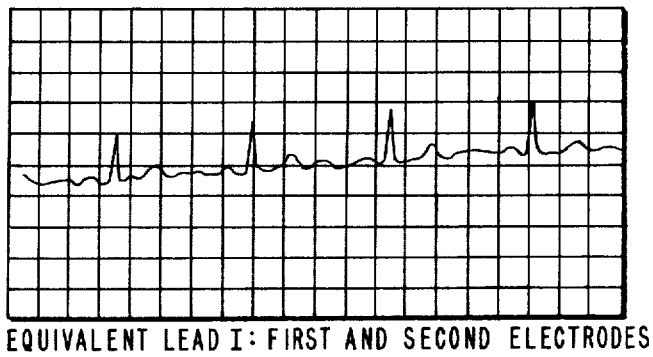
EQUIVALENT LEAD I: FIRST AND SECOND ELECTRODES

STANDARD LEAD $CM_5$

LEAD $CM_5$: FIRST AND THIRD ELECTRODES

STANDARD LEAD III

EQUIVALENT LEAD III: SECOND AND THIRD ELECTRODES

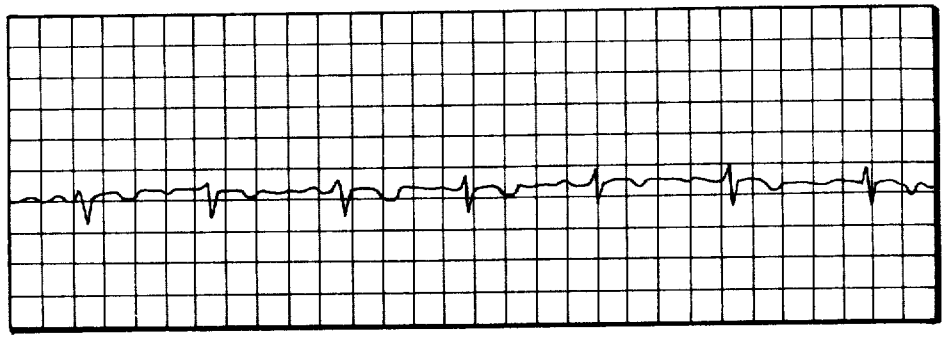
FIG.-5A
STANDARD LEAD $V_1$
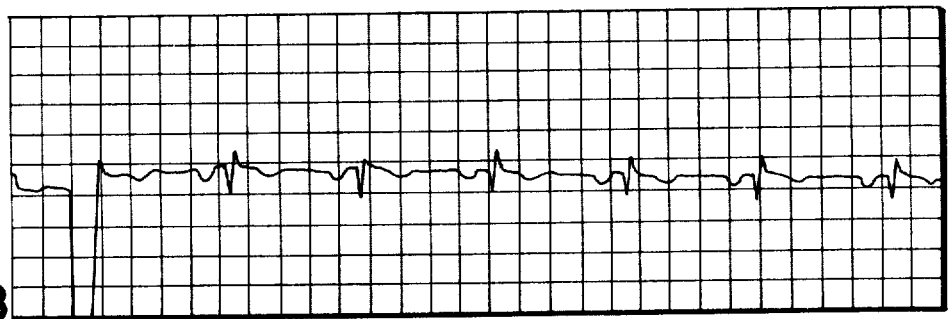
FIG.-5B
BATTERY VOLTAGE INDICATION
EQUIVALENT LEAD $V_1$ : SECOND AND FOURTH ELECTRODES
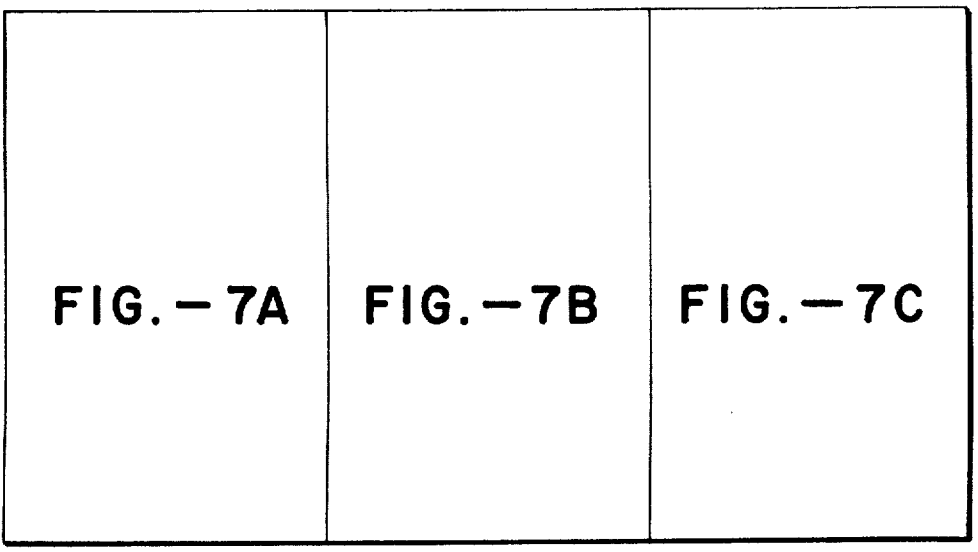
FIG. — 6

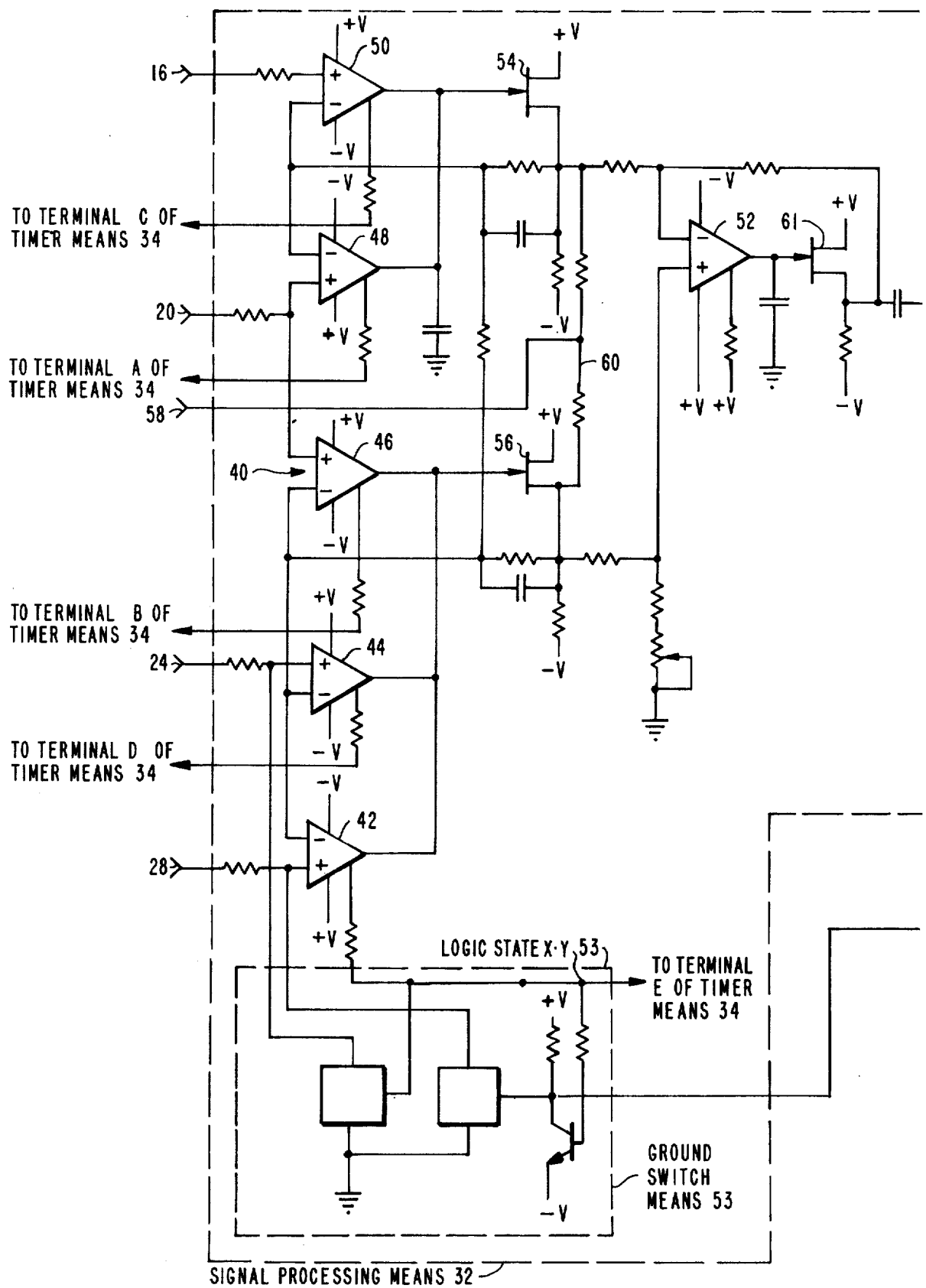
FIG.—7A

PORTABLE CARDIAC MONITORING SYSTEM AND METHOD

This is a continuation of application Ser. No. 265,473, filed June 23, 1972 and now abandoned.

BACKGROUND OF THE INVENTION

1. Field of the Invention

The invention concerns itself with biological systems and methods such as for monitoring cardiac action of a patient physically distant from stationary facilities for measuring and analyzing cardiac data.

2. Description of the Prior Art

The value of portable biological monitoring devices which sense and transmit cardiac information to distant facilities for processing, display, and analysis has become increasingly recognized. In addition to the many advantages of existing nonportable monitoring devices having the capability of providing cardiac information to distant facilities, such as providing access to sophisticated research and treatment centers and permitting tests to be conducted in physicians' offices, it has been recognized that portable devices would have significant favorable aspects. Such systems may be activated at any time by the user when he senses symptons of cardiac malfunction or may be operated routinely in accordance with a prescribed program. These functions may be carried out with minimum disruption of the routine of the patient.

There have, however, been many problems in implementing portable cardiac monitoring devices. The stationary monitoring systems are not adaptable to being made portable. These systems generally comprise a standard EKG device equipped with means for transmitting or storing cardiac information for transfer to a distant medical facility. These standard systems are predicated upon isolating the patient from his normal activities and environment. For example, the patient must be isolated from common 60 cycle electrical sources to avoid common mode disturbance of the recorded cardiac signals. The patient must be muscularly relaxed to avoid muscular artifacts in the reading and must be motionless to eliminate error due to static electrical charge. The patient's skin must be specially prepared, usually by abrasion of the epidermal layer, to obviate the problem of artifacts due to variations in skin resistance. Moreover, existing systems utilize a large number of patient contact electrodes interconnected to one another to obtain patterns of cardiac potential related to the conventional EKG data. The interconnections among the electrodes are in some cases through resistors and form a complex network along the patient's body. The expense and bulk of such complex systems have been a substantial problem.

A frequently seen portable system is one having a minimal number of leads to obviate somewhat the problems of unwieldiness and complexity of lead structure of the abovediscussed devices. Such simple systems pay a substantial price, however, in diminution of information. Moreover, there has been no significant attack on the problems, which arise particularly frequently with ambulatory patients, of common mode vulnerability and instability of signal due to variations in skin resistance of the patient. Moreover, existing systems suffer from the drawback that the electrodes which they utilize are often affixed over muscle or other tissue and thus introduce muscular artifacts into the sensed potentials from the heart for the non-muscularly relaxed patient. Existing systems further tend to lack the versatility achieved by combining EKG or cardiac monitoring with monitoring of a pacemaker.

Therefore, there has been a recognized but unfulfilled need for a portable cardiac action monitoring system, having the capability of providing substantial cardiac information, as well as pacemaker information, which is not compromised in its ability to process cardiac signals by ambient electrical noise, by fluctuations in skin resistance of the patient or by muscular artifacts and is at the same time economical and sufficiently comfortable, convenient, compact, and lightweight to meet the physical and social needs of ambulatory patients utilizing the device. Monitoring systems which fulfill these requirements must also, if possible, provide transmittable signals for conventional communications systems (e.g. telephones) that can be used after demodulation for recordation by conventional means, such as an EKG recorder or tape recorder.

SUMMARY OF THE INVENTION

Systems and methods are provided for monitoring biological actions such as the cardiac and pacemaker action of a patient, physically removed from stationary facilities for measuring and analyzing cardiac data. The system which is compact, lightweight, and readily portable, includes a plurality of electrodes conveniently affixable to the chest region of the patient at selected, bony portions thereof to sense potentials generated in conjunction with the patient's cardiac action. The electrodes are arrayable in the X, Y and Z planes so that potentials sensed by selected bipolar pairs of a total of no more than four electrodes provide a very large percentage (up to 90%) of the information obtainable by conventional 12 lead EKG techniques as well as some of the critical precordial leads. The electrodes, which are not connected to one another across the body of the patient, are electrically connected to signal processing means for combining and preparing signals, generated by the potentials sensed by selected pairs of electrodes, for serial or multiplex transmission to a distant facility. The characteristic spike of the pacemaker potential can be readily extracted from a composite signal and provides a test of the effectiveness and remaining life of the pacemaker battery. Means are also provided for maintaining a selected signal for as long an interval as desired.

The signal processing means is of very high electrical impedance in relation to the impedance of the patient and thus minimizes errors and artifacts due to fluctuations in skin resistance of the patient, thereby obviating the need for preparatory treatment of the skin of the patient. The signal processing means includes a sequential control for processing currents derived from the potentials sensed by the electrodes in selected pairs, for selected intervals. The signal sequence is modulated for multiplex transmission — by radio, telephone, or other convenient means — of the combined electrode pair or lead readings. The serially presented data contain substantially 90% of the data available from the conventional EKG.

Switch settling means included in th signal processing means permits rapid switching between electrode pairs. The signal processing means further includes means for selectively grounding one of the non-accessed electrodes during each period of conduction of the selected electrode pairs, providing a common DC return to the patient.

The potential of the power source, a DC battery, is reflected in a separate signal transmitted as a marker, within the cycle of lead switching. Approaching end of battery life is indicated by a sharply defined and easily discernible change in the battery signal.

Particular elements in the signal processing means contribute to sensitivity, stability and high impedance operation of the system. Signals from pairs of electrodes pass through buffer amplifiers which are selectively activated to permit signal conduction into the signal processing system, through a differential amplifier to a voltage controlled oscillator (VCO) arranged as an FM modulator, the modulated signals driving a speaker. The buffer means input impedance is enhanced by coupled field effect devices which act as source followers thus significantly reducing the load on the buffer imposed by subsequent circuitry. The VCO means, which is highly sensitive and stable, also contributes to high impedance operation. The VCO means comprises matched pairs of differential amplifiers regeneratively connected to amplifying transistor elements. Aspects of circuitry and operation such as time-sharing and sequenced use of circuit elements contribute to substantial economies. Means are provided for suppression of VCO frequencies which interact adversely with telephone systems.

BRIEF DESCRIPTION OF THE DRAWINGS

FIG. 1 is a perspective view of a plurality of electrodes in electrical contact with a patient and coupled to a signal processing system in accordance with the invention;

FIGS. 2-5 are simplified graphical recorder charts (designated A) of cardiac action obtained from conventional EKG measurement, as compared to equivalent charts (designated B) of cardiac action obtained by measurements in accordance with the invention;

FIG. 6 is a diagram of the manner in which the various circuit portions of FIGS. 7A, 7B and 7C joint together to form a complete circuit; and FIGS. 7A, 7B and 7C, taken together, comprise a schematic circuit diagram of a cardiac monitoring system in accordance with the invention.

DETAILED DESCRIPTION OF THE INVENTION

Figure 3A:
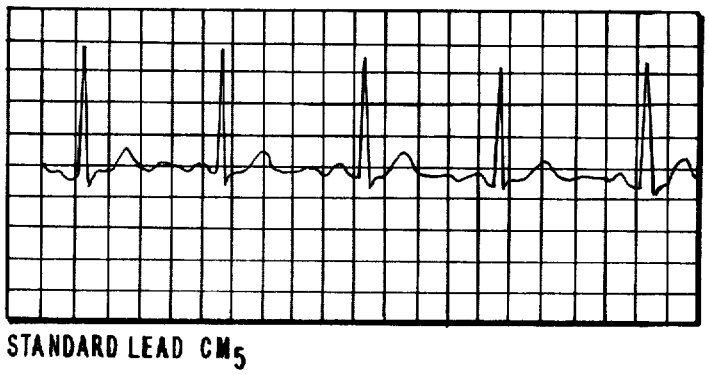
Figure 3B:
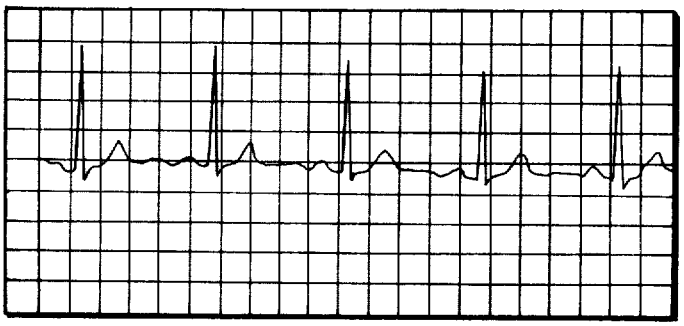

As shown in FIG. 1, a plurality of electrodes are attached in electrical contact with the body 10 of a patient, and each is coupled by a conductor 12 to a small battery-powered cardiac monitor 14 in accordance with the invention. A first electrodoe 16 is affixed to the right side of the manubrium 18 of the patient. A second electrode 20 is affixed to the outer left clavicle 22 of the patient. A third electrode 24 is attached in the area of the "$V_5$ position" along the ribs 26 of the patient. The $V_5$ position is recognized in medical terminology as a specific rib position and this designation is used hereafter. A fourth electrode 28 is affixed to the patient in the area of the "$V_1$ position" 30, conventionally used to designate the right side of the sternum, fourth rib. The electrodes are thus arrayed in the X, Y and Z planes. (In the medical profession the human chest is considered as having X, Y and Z planes for purposes of EKG connection. The X and Y axes of such a coordinate system are considered as extending across the width and along the height of the chest respectively, while the Z axis extends into the chest.) It should be noted that, of course, the positions of the electrodes could be altered by, for example, substituting the $V_2$ or $V_3$ positions for the $V_1$ position or by disposing the first and second electrodes at other points to the right and left, respectively, of the upper sternum.

FIGS. 2-5 are comparative graphical recorder outputs taken for various electrode pairs with conventional systems and systems in accordance with the invention. As shown in FIG. 2, the graph of the signal representing the difference in potential between the first electrode 16 and the second electrode 20 (FIG. 2B) corresponds closely to the output (FIG. 2A) provided by the conventional horizontal first lead (standard lead I) of the standard electrocardiogram. (In the medical profession the term "lead" means "a signal generated by one 'exploring' electrode and one or a combination of other electrodes"; for example, many of the classical EKG "leads" comprise three electrodes connected in parallel to yield a signal in conjunction with a fourth electrode; the term is frequently used in this manner herein as determined from the context).

Figure 4A:
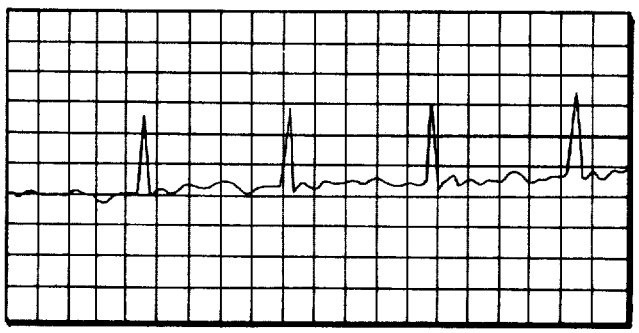
Figure 4B:
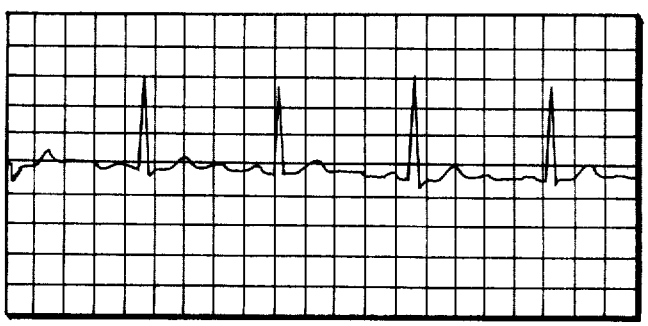

The difference in potential between the first electrode 16 and the third electrode 24 (FIG. 3B) comprises the known $CM_5$ lead (FIG. 3A) sometimes used in stress testing (the manubrium to $V_5$ position) and provides further information comprising substantially 90% of the ischemic indications on the standard 12 lead EKG. This lead provides a combination of the anterior-posterior lead $V_5$ and the transverse vertical-horizontal lead $aV_F$. The difference in potential between the second and third electrodes 20, 24 (FIG. 4B) provides information equivalent to that provided by the conventional vertical EKG lead III (FIG. 4A). The potential difference between the second electrode 20 and the fourth electrode 28 provides an anterior-posterior reading closely equivalent to the conventional $V_1$ lead (FIGS. 5A, 5B). The fourth electrode 28 could be moved to the $V_2$ or $V_3$ positions and would yield anterior-posterior cardiac data together with significant precordial information. Thus, each of the first three electrodes performs as an element of two different leads, and the information obtainable from the electrode array is consequently varied, extensive, and significant.

The various electrode combinations provide over approximately 90% of the ischemic indications normally shown in a complete 12 lead EKG record. The second-fourth electrode combination provides an excellent means for determining atrial disorders and for distinguishing between ventricular atrophy and abberation. Thus in accordance with the invention a convenient array of a relatively small number of electrodes provides information substantially equivalent to that provided by the conventional EKG system, which employs a complex and cumbersome network of electrodes. All the electrodes can be affixed over bony portions of the body of the patient and thus are not subject to sensing irregular potentials due to muscular artifacts which obscure, sometimes to a considerable degree, the cardiac data desired. The electrodes are placed on the patient's body so that they are conveniently accessible to the patient.

Figure 7B:
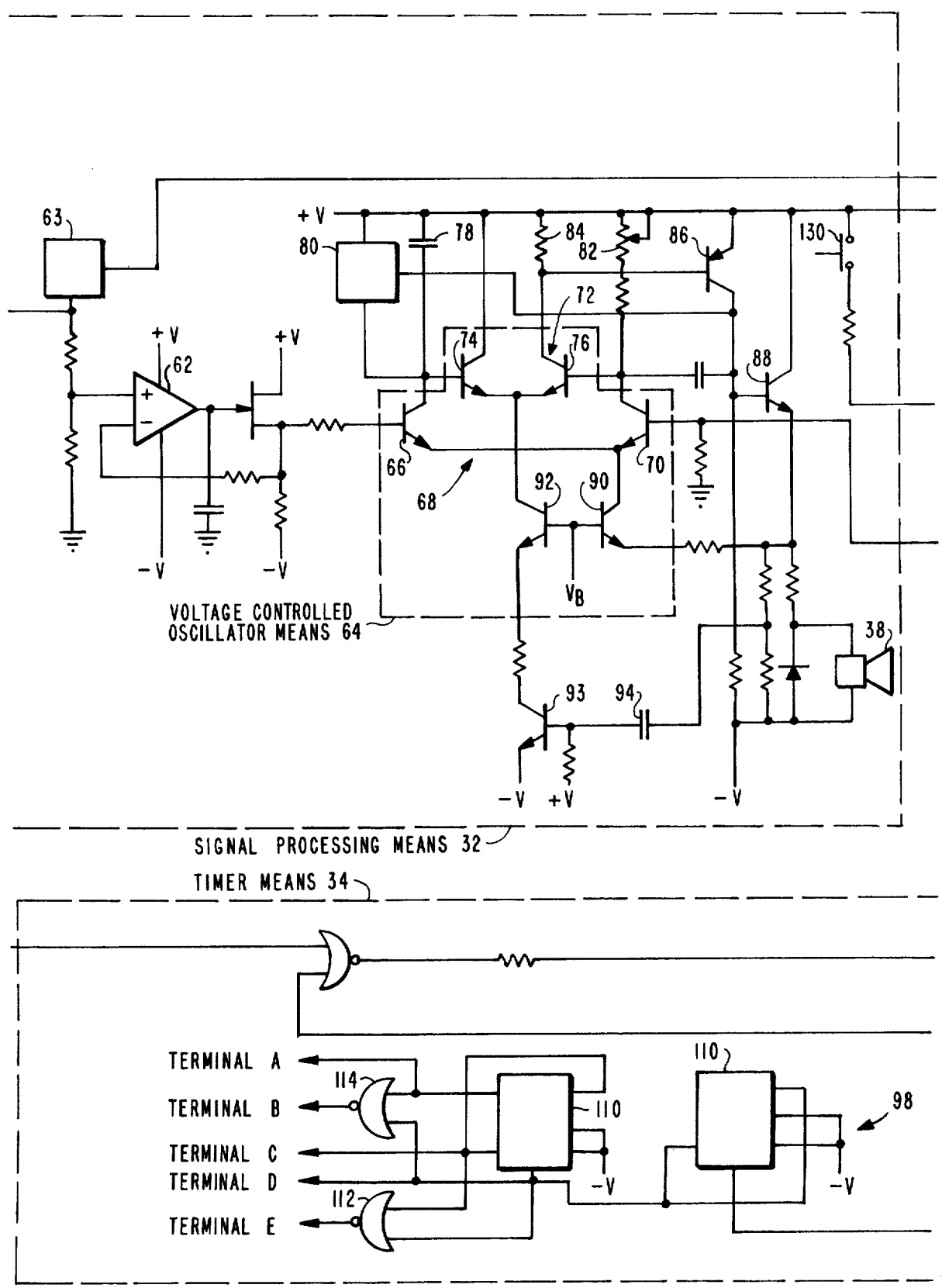
Figure 7C:
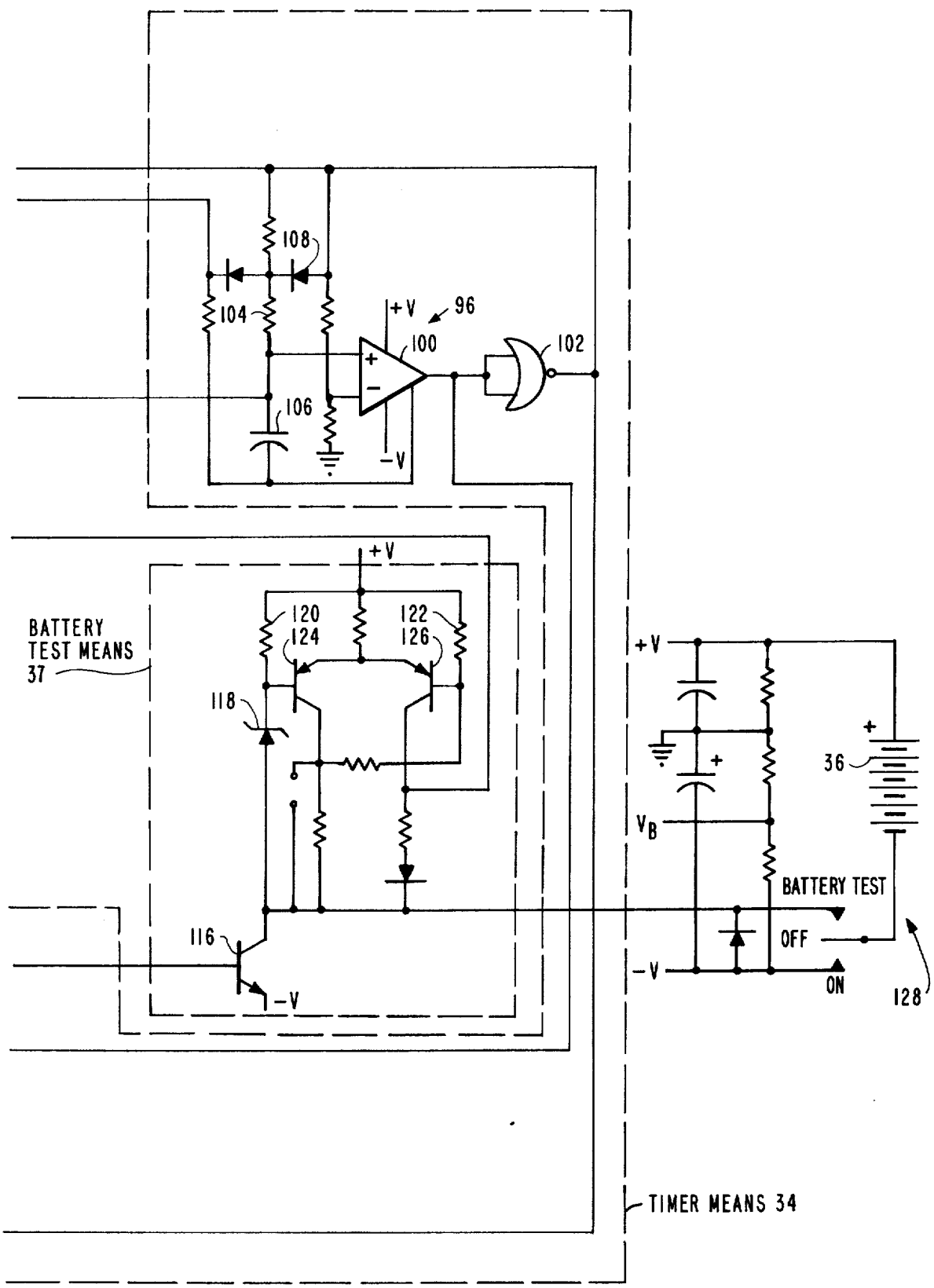

As shown in FIG. 7A, the electrodes are connected to signal processing means 32, which amplifies and otherwise prepares electrical currents due to the potentials sensed by the electrodes for transmission to a distant facility having the capability of graphing and analyzing the cardiac data from the patient. The signal processing means 32 has very high impedance in relation to the impedance of the patient, typically 2,000 megohms at 1 cps and 500 megohms or more at 120 cps as compared with 150,000 ohms or less for the patient. Thus, variations in skin resistance of the patient have little or no effect on the graphical record of the patient's cardiac data.

Control means 34 is connected to the signal processing means 32 and provides signals to the signal processing means 32 so that the means 32 is conductive with respect to selected pairs of electrodes for selected time intervals and in a chosen sequence to form a complete cycle for multiplex transmission. For example, a practical sequence is Lead I (second electrode minus first electrode), Lead III (third electrode minus second electrode), Lead $CM_5$ (third electrode minus first electrode), and $V_1$ lead (fourth electrode minus second electrode). A DC power source 36 in the form of a battery is coupled to the signal processing means 32.

At a preselected point in the multiplex cycle the control means 34 provides a signal activating sync or battery test means 37 to provide a signal to the signal processing means 32. This permits a sync or battery test impulse to pass through the signal processing means 32 to the recording facility. The battery impulse graph thus acts as a marker to determine where in the cycle transmission is begun to be recorded as well as providing a means for monitoring the effectiveness of the battery.

The control means 34 further provides signals to the signal processing means 32 so that at any time when the signal processing means is conductive for a pair of electrodes one of the remaining, nonconductive electrodes acts as a ground which, through the patient, provides bias potential for elements at the input of means 32 and thus facilitates high input impedance as noted below.

The signal processing means 32 contains electronic elements for processing currents due to the differences in potentials between given pairs of electrodes for transmission via a speaker 38 and a transmitter to a distant recording and analyzing facility. Under the influence of the control means 34, pairs of a plurality of buffer amplifiers 40 included in means 32 are activated to be conductive with respect to currents from selected pairs of the electrodes 10. In the particular configuration shown there are five buffers: a first buffer 42 connected to the fourth electrode 28, a second buffer 44 connected to the third electrode 24, a third buffer 46 connected to the second electrode 20, a fourth buffer 48 connected to the second electrode 20, and a fifth buffer 50 connected to the first electrode 16. In the particular configuration shown herein, whenever the signal processing means 32 is receiving current from the electrodes 10, one of the buffers 42, 44, 46 is on and one of the other two buffers 48 and 50 is also on. The first, second and third buffers 42, 44, 46 buffer signals entering the non-inverting end of a differential amplifier 52; the fourth and fifth buffers 48, 50 buffer signals entering the inverting and of the amplifier 52.

For purposes of exposition, the currents due to potentials sensed by the first electrode 16 and the second electrode 20 will be specifically considered. These currents exist when the control means 34 activates buffers 46, 50 to conduct current to the signal processing means 32. At the same time, ground switch means 53 is activated so that the fourth electrode 28 acts as ground. The currents from the first and second electrodes 16, 20 pass to field effect transistors 54, 56, respectively, where the currents provide bias. The field effect transistors 54, 56 are connected between plus and minus potential sources ($\pm$ V). In effect the field effect transistors 54, 56 at this time comprise functional elements of buffer combinations including the buffers 46, 50 respectively. The field effect transistors, in this view, act as effective outputs for their respective buffers. The field effect transistors operate at high gain with very low input current in contrast, for example, to a junction type transistor. Thus, the field effect transistors optimize the high impedance characteristics of the buffers and enable the high impedance of the signal processing means 32 to exist without sacrifice of gain or accuracy. In a typical example, the gain times open loop impedance of the signal processing means is 2,000 megohms.

The outputs of the field effect transistors 54, 56, are connected to the differential amplifier 52 where a shield 58 encloses wires between the buffers and the patient to protect the system from common mode signals. The effect of the capacitance between the shield and wires is negated by a voltage divider 60 to which the shield and the buffer inputs are connected. The shield and the input wires are consequently at the same potential, thus neutralizing the effect of the capacitance between the shield and wires.

The effective output of the differential amplifier 52, field effect transistor means 61 is coupled to interstage buffer means 62 and analog switch 63, which is excited by control means 34 to facilitate rapid settling of signals following switching of electrode pairs.

The output of interstage buffer amplifier 62 is connected to a voltage controlled oscillator means 64 and specifically to the base of a first transistor 66 of a first transistor pair 68 of the VCO 64. The VCO provides further gain with high inherent sensitivity and stability. Substantial economies are achievable through the use of the VCO arrangement shown vis-a-vis the more conventional integrating capacitors or operational amplifiers which could be used for the same purpose. A second transistor 70 is included in the first differential amplifier pair 68. A second differential amplifier pair 72 is included in the VCO 64 and comprises first and second transistors 74, 76 whose bases are coupled to the collectors of the first differential amplifier pair 68. The collector of transistor 66 is also coupled to a pair of parallel circuit elements, a capacitor 78 and an analog switch 80, as is the base of the transistor 74. The collector of transistor 70 is coupled to a resistor 82 as is the base of transistor 76. Coupled to the collector of transistor 76 are a resistor 84 and the base of PNP means 86. The collector of PNP means 86 connects to the analog switch 80. The elements 74, 76, 78, 80, and the combination of elements 82, 84, and 86 are connected in parallel to the source of positive potential 36. Also in parallel with these elements is NPN means 88, whose base is connected with analog switch 80 and with the collector of PNP means 86.

The emitter of NPN means 88 connects to speaker 38, whose output is coupled to a transmission means (not shown), and to transistor means 90 whose collector is coupled to the emitters of the first differential amplifier pair 68. Transistor means 92 is coupled at its base to the base of transistor 90 and to a bias voltage, V, and at its collector is coupled to the emitters of the second differential amplifier pair 72. The emitter of transistor 92 is coupled to a transistor 93 and a differentiating capacitor 92 coupled thereto, which together comprise a strobe means for suppressing frequencies adverse to telephone networks (above 2450 cps).

In operation, when only current due to the voltage source and sink exist in the VCO an emitter current is established at the terminals of the first differential amplifier pair 68 and is equally shared at the terminals. The current charges capacitor 78 and passes through resistor 82. When the potentials at the terminals are equal and the hold off period of the strobe, which operates as a one-shot, has elapsed, the second differential pair 72 senses the equality and provides bias current to PNP means 86. The PNP means 86 responds with current to NPN means 88 which provides current to drive the speaker 38, simultaneously removing emitter current of differential pair 68 through transistor 90 and providing a regenerative effect due to to collapse of the established potential of resistor 82. Current is provided to the differentiating capacitor 94 to restore the potential required for a subsequent cycle. During this time capacitor 78 tends to retain its charge while resistor 82, of course, does not and thus in differential pair 72 current imbalance is produced which provides positive feedback. The analog switch 82 is set to discharge the capacitor 78 to a predetermined voltage to reset the cycle.

When there is modulation, that is when a cardiac potential difference signal is received from the interstage buffer amplifier 62, an imbalance is created in the emitter currents at the terminals of the first differential amplifier pair 68 producing differential charging of the capacitor 78 and thus a gain which drives the speaker 38. Therefore, signals are transmitted as deviations from a base signal.

The control means 34 includes a free running multivibrator 96 and a counter 98. The multivibrator 96 clocks the counter 98 and in a typical application provides an eight second delay and a .2 second pulse so that, every eight seconds, a pulse of 2/10th second duration occurs. The leading edge of the pulse increments the counter. An amplifier 100 of the multivibrator 96 drives a gate 102 which functions to increase $\Delta v/\Delta t$ of the transition time. The timing is accomplished by series-connected resistor means 104 and capacitor means 106. The amplifier 100 operates effectively as a voltage comparator, and the pulse is applied to the effective negative terminal on the amplifier. The effective positive terminal of the amplifier in effect operates as a voltage divider operating at 50% of the applied voltage or 0.7 of one time constant per RC. Diode means 108, connected to the inverting end of the amplifier 100, bypasses the resistor means 104 to permit deviation from a symmetrical square wave.

The counter 98 operates as a ripple counter and includes a pair of flip flops 110 connected as primary and slave flip flop or memory. The two flip flops thus comprise a four state ripple counter with the second state being derived from the terminal outputs of the first state. The states are decoded by gates 112, 114 and the appropriate current is applied to the input buffers 40 corresponding to the desired logic state. In the specific embodiment shown, terminals A, B, C, D, and E couple to the buffers 40 as follows: terminal A (corresponding to logic state Y of the counter 98) to buffer 48; terminal B (logic state X$\overline{Y}$) to buffer 46; terminal C (logic state $\overline{Y}$) to buffer 50; terminal D (logic state $\overline{X}$) to buffer 44; and terminal E (logic state XY) to buffer 42. Terminal E also couples to the ground switch 53 which closes at logic state XY and $\overline{XY}$. This permits grounding of one non-accessed electrode during conduction by each selected pair of electrodes. Thus, four distinct logic states exist corresponding to the four different cardiological leads described above. Each pair transmits for eight seconds per cycle with approximately 2/10th of a second reset time during which the non-symmetrical square wave is applied to the means 63 to effect switch settling.

At a selected point in the cycle a sync or battery test signal is transmitted. This signal acts as a marker as well as an indicator of approaching end of life for the battery and, in the depicted system, is generated during the reset pulse preceding the fourth count as seen in FIG. 5B. Through gate 112, the fourth logic state of the counter 100 activates the battery test means 37. The battery test means 37 comprises a saturable switch transistor 116 which drives a voltage reference zener diode 118 and an adjustable voltage divider comprising resistors 120, 122. The resistors are connected to a differential pair of transistors 124, 126. Transistor 126 is connected to the base of transistor 70 in the VCO 64. The battery test is performed at twice nominal load in order to verify battery impedance.

The voltage divider is adjusted so that, if the battery voltage should fall below a predetermined value — 7.4 volts in a specific example — current will pass to the transistor 70 and thus cause the output frequency to decrease. Conversely, when the voltage is above the preselected value, current would be drawn from the base of transistor 70 and the output frequency would increase, indicating an acceptable battery condition. The system may be arranged so that the battery test signal is audible to the patient.

A local battery test feature is provided to permit the patient to test the battery at any point in the cycle. In a power switch means 128, there are three positions of a power switch, "on", "off", and "battery test". The battery test terminal connects the (−) terminal of the battery to the zener diode 118 so that upon activation of the battery test terminal of the power switch the battery test impulse overrides all other signals to the VCO.

Also provided in accordance with the invention are means for continuing the transmission of desired signals from a given pair of electrodes beyond the time allotted to that electrode pair in the cycle of lead switching provided herein. A hold switch 130 is disposed between +V and the timer 96 so that one lead is connected at the output of capacitor 106 and the other is connected to the voltage means 36. When closed, the switch 130 disables the timer so that no lead switching can occur. This feature is advantageous for use in response to a request from the distant EKG analysis facility for further cardiac signal transmission from a particular lead.

In accordance with the invention, the action of a pacemaker affixed to the patient may be monitored. The periodicity of the pacemaker impulse and the time interval between the impulse and ventricular activation are both indications of pacemaker effectiveness. The pacemaker spike impulse is distinctive and can be readily recognized within, and separated from cardiac data transmitted by systems in accordance with the invention; thus, the effectiveness of the pacemaker can be readily monitored.

At the distant center to which the cardiac action signals are transmitted, the signals are received, demodulated, and displayed by conventional means (not shown). The display may be by oscilloscope, magnetic tape, EKG recorder, pacemaker condition displays, or other standard display means.

The described embodiments contribute specific examples of systems in accordance with the invention and do not by themselves limit the invention, which is defined by the following claims.

What is claimed is:

1. A system for processing electric currents due to potentials accompanying cardiac action of an ambulatory patient or electrical impulses from a pulse generator designed to pace the heart for multiplex transmission to monitoring facilities, comprising: a plurality of electrodes adapted to electrically contact the body of a patient, amplifying means for amplifying signals fed thereto, means coupled to the amplifying means for providing an indication of information carried by amplified signals from the amplifying means, a plurality of buffer amplifier means coupled between the amplifying means and the electrodes, and sequencing means coupled to and controlling the buffer amplifier means, the sequencing means including means for rendering selected ones of the buffer amplifier means conductive to pass signals to the amplifying means and for simultaneously coupling a selected one of the buffer amplifier means as a ground connection in response to potentials from selected ones of said electrodes at selected intervals.

2. The invention as set forth in claim 1 wherein there are four said electrodes and wherein said buffer amplifier means comprises five buffer amplifiers, the first electrode being adapted to be attached to the manubrium of a patient and electrically connected to a first one of the five buffer amplifiers, a second electrode being adapted to be attached to the outer left clavicle of a patient and connected to second and third ones of the five buffer amplifiers, a third electrode being adapted to be disposed in the region of the $V_5$ position and connected to a fourth one of the five buffer amplifiers, and a fourth electrode being adapted to be disposed in the region of the $V_1$ position and connected to a fifth one of the five buffer amplifiers, and further including ground switch means coupled to the sequencing means and the buffer amplifiers to ground the fifth buffer amplifier when the first and second buffer amplifiers are conductive.

3. The invention as set forth in claim 1 further including hold means for preventing operation of the sequencing means to continue passage of signals by the buffer amplifier means to the amplifying means in response to potentials from selected ones of the electrodes.

4. The invention as set forth in claim 1 further including battery means coupled to power said system, battery test means, and oscillator means, the oscillator means being coupled to the output of said amplifying means, the battery test means being coupled to the oscillator means and to the battery means for providing a signal to the oscillator means indicating the condition of the battery means.

5. The invention as set forth in claim 4 further including override means coupled to said battery test means for overriding all other signals to said oscillator means with said battery test signal.

6. A cardiac monitoring system comprising a plurality of electrodes adapted to be coupled to the body of a patient to derive signals, a voltage controlled oscillator, timing means for gating the signals from the electrodes to the voltage controlled oscillator, the voltage controlled oscillator generating output signals representative of the signals derived from the electrodes and means responsive to the output signals for providing an indication of information carried by said output signals, a power supply for powering the system, and an arrangement for periodically generating a signal representing the relative strength of the power supply comprising threshold means, means coupled between the timing means and the threshold means for periodically actuating the threshold means, means coupling the threshold means to the power supply, the threshold means including means which is operative when actuated to provide a power supply test signal to the voltage controlled oscillator if the strength of the power supply is at least equal to a predetermined threshold level, the voltage controlled oscillator including means responsive to the power supply test signal for generating an output signal having a frequency representing the power supply test signal.

7. The invention defined in claim 6, wherein the power supply test signal comprises a pulse having an amplitude representing the strength of the power supply.

8. A system for sensing and amplifying electrical potentials generated in conjunction with cardiac activity or activity from a pulse generator designed to pace the heart for transmission to distant monitoring facilities comprising: signal processing means, a plurality of electrodes connected to said signal processing means, the signal processing means including means for receiving and amplifying currents generated in conjunction with said potentials, control means for controlling said signal processing means, means connecting the control means to said signal processing means to activate the signal processing means at selected intervals and in selected sequences to conduct currents due to potentials sensed by combinations of the electrodes, means for providing an indication of information carried by currents amplified by said means for receiving and amplifying, power source means coupled to power the signal processing means and the control means, the power source means comprising a direct current power source and power source test means coupled to the power source for receiving a signal from the power source and for processing the power source signal to generate a power source status output signal to said signal processing means for transmission to said monitoring facilities at selected time intervals, said control means including means for activating the power source test means to generate a power source status output signal at selected times during cycles of operation of the system, and further including means for activating the power source test means to generate a power source status output signal at any time during one of the cycles of operation of the system whenever initiated by an operator.

9. A system for processing electrocardiac potentials for transmission to facilities for recording and analyzing such signals comprising: electrode means adapted to be affixed in a selected pattern to the body of a patient for sensing and conducting signals produced by electrocardiac potentials, electronic means coupled to the electrode means for amplifying and multiplexing said signals, the electronic means including a plurality of amplifier means, each of the amplifier means comprising a field effect transistor coupled to amplify signals from the electrode means, a plurality of gating means coupled to the electrode means for selectively coupling the electrode means to the amplifier means, each of said gating means comprising a buffer amplifier and timing means for controlling the buffer amplifier, said plurality of amplifier means providing high gain amplification of signals from the electrode means, a differential amplifier coupled to the amplifier means for generating signals representing the difference between signals amplified by the amplifier means, oscillator means coupled to generate a signal having a frequency determined by the signals representing the difference, said oscillator means comprising a voltage controlled oscillator, indicator means coupled to the oscillator means for providing an indication of information carried by the signal generated by the oscillator means and buffer means controlling application of the signals representing the difference to the oscillator means.

10. A system for receiving and transmitting cardiac signals associated with the heart action of a patient or his implanted pulse generator designed to pace the heart comprising: a plurality of electrodes for measuring potentials associated with heart action of a patient, gain means and control means, means connecting the electrodes to the gain means, the gain means being controlled by the control means to conduct current from selected combinations of electrodes at selected intervals, the gain means including amplifier means and voltage controlled oscillator means, means connecting the voltage controlled oscillator means to the output of the amplifier means, means coupled to the voltage controlled oscillator means for providing an indication of information carried by signals from the voltage controlled oscillator means, the voltage controlled oscillator means including first and second differential amplifier means, each differential amplifier means comprising two transistors, each having a base, an emitter and a collector, means connecting the base of a first transistor of the first differential amplifier means to the output of the amplifier means, means for providing the collector of the first transistor and the base of a first transistor of said second differential amplifier means with the same potential, the base of the second transistor of the first differential amplifying means being coupled to ground, means connecting the collector of the second transistor of the first differential amplifying means to the base of the second transistor of the second differential amplifying means, means for providing the emitter reactance means, an analog switch, means connecting the collector of the first transistor of the first differential amplifying means to the reactance means and to the analog switch, a source of positive potential, means connecting said analog switch and reactance means to the source of positive potential, resistance means, means connecting the collector of the second transistor of the first differential amplifying means to the resistance means, means connecting the resistance means to the source of positive potential, means connecting the collectors of the first and second transistors of the second differential amplifying means to the source of positive potential, means connecting the emitters of the first and second transistors of the first and second differential amplifying means to a source of negative potential, a PNP transistor having a base, an emitter and a collector, means connecting the collector of the second transistor of the second differential amplifying means to the base of the PNP transistor, means connecting the emitter of the PNP transistor to the source of positive potential, the second differential amplifying means being set to provide bias current to the PNP transistor when potentials at the bases of the transistors comprising said second differential amplifying means are equal, an NPN transistor having a base, an emitter and a collector, means connecting the collector of said PNP transistor to the base of the NPN transistor, means connecting the collector of the NPN transistor to the source of positive potential, and means connecting the emitter of said NPN transistor to the emitters of the transistors comprising said first differential amplifier means to the emitters of the transistors comprising said second differential amplifying means.

11. The invention as set forth in claim 10 further including a power source, comprising battery means coupled to power said system, and battery test means for providing a signal indicating the effectiveness of the battery means, means coupling the battery test means to the battery means and to the base of the second transistor of said first differential amplifier means of said voltage controlled oscillator means.

12. The invention as set forth in claim 10 further including means coupled to the emitter of the first transistor in said second differential amplifier means for limiting the maximum frequency output of said voltage controlled oscillator means.

13. The invention as set forth in claim 12 further including first and second conduction transistors each having an emitter, a collector and a base, means connecting the emitter of said first conduction transistor to the emitter of said NPN transistor and the collector of the first conduction transistor to the emitters of the transistors comprising the first differential amplifier means, means connecting the second conduction transistor means between the emitters of said transistors comprising the second differential amplifier means and said means for limiting the maximum frequency output of said voltage controlled oscillator means, and means for coupling the bases of the first and second conduction transistor means together.

14. The invention as set forth in claim 10 wherein said analog switch is set to discharge said reactance means when there is no emitter current in the first differential pair.

15. A system for sensing and amplifying electrical potentials generated in conjunction with cardiac activity or activity from a pulse generator designed to pace the heart for transmission to distant monitoring facilities comprising: signal processing means, a plurality of electrodes connected to said signal processing means, the signal processing means including means for receiving and amplifying currents generated in conjunction with said potentials, control means for controlling said signal processing means, means connecting the control means to said signal processing means to activate the signal processing means at selected intervals and in selected sequences to conduct currents due to potentials sensed by combinations of the electrodes, means for providing an indication of information carried by currents amplified by said means for receiving and amplifying, power source means coupled to power the signal processing means and the control means, the power source means comprising a direct current power source and power source test means coupled to the power source for receiving a signal from the power source and for processing the power source signal to generate a power source status output signal to said signal processing means, means for transmitting the power source status output to said monitoring facilities at selected time intervals, said control means providing signals to said signal processing means to ground a selected one of the other electrodes during the state of conduction for each pair of electrodes.

16. A cardiac monitoring system comprising a plurality of electrodes adapted to be coupled to the body of a patient for providing signals, means for generating an output signal, timing means for gating signals from the electrodes to the means for generating an output signal, the means for generating an output signal being operative to generate output signals representing the signals derived from the plurality of electrodes and providing the output signals to indicator means and comprising a voltage controlled oscillator including means including a first pair of transistors coupled to form first differential amplifier, the first differential amplifier being normally balanced, means coupling the first differential amplifier to be unbalanced by the presence of the signals derived from the electrodes, a capacitor and a resistor coupled between a common power supply and different ones of the first pair of transistors, means including a second pair of transistors coupled to form a second differential amplifier, means coupling the transistors of the second pair to different ones of the transistors of the first pair to provide operation of the second differential amplifier in response to the first differential amplifier, an output, at least one amplifier coupled between the second differential amplifier and the output, means coupled between the at least one amplifier and the first differential amplifier for controlling the current in the first pair of transistors, and means for periodically discharging the capacitor.

17. A biological monitoring system comprising:
   sensor means for generating at least two sensor signals in response to biological actions;
   means coupled to receive the sensor signals and providing a high input impedance for each said sensor signal, said means including amplifier means for generating intermediate signals in response to the sensor signals, and a field effect transistor for generating final signals in response to the intermediate signals, the field effect transistor being coupled to the amplifier means;
   processing means responsive to the final signals for processing said signals and including differential amplifier means coupled to the field effect transistor for providing a differential signal in response to the difference between the final signals, and voltage controlled oscillator means for providing a signal which varies in frequency in response to the differential signal;
   indicator means responsive to the processed signals for providing an indication of information carried by the processed signals;
   conductor means coupled to pass the sensor signals to the means providing a high input impedance;
   shield means arranged to shield the conductor means against common mode signals; and
   means coupled to said shield means for exciting the shield means with a shield signal relating to the sensor signals to reduce capacitive coupling between the conductor means and the shield means.

18. The invention as set forth in claim 17, wherein there are four of said sensor means and wherein said amplifier means comprises five buffer amplifiers, the first sensor means being adapted to be attached to the manubrium of a patient and electrically connected to a first one of the five buffer amplifiers, the second sensor means being adapted to be attached to the left clavicle of a patient and connected to second and third ones of the five buffer amplifiers, the third sensor means being adapted to be attached in the region of the $V_5$ position and connected to a fourth one of the five buffer amplifiers, and the fourth sensor means being adapted to the attached in the region of the $V_1$ position and connected to a fifth one of the buffer amplifiers, and further including sequencing means coupled to and controlling the buffer amplifiers to sequentially render selective ones of the buffer amplifiers conductive, said sequencing means being operative to select two of the buffer amplifiers to be connected to the differential amplifier means while selecting a third of the buffer amplifiers to be connected as a ground means, and thereafter selecting another two of the buffer amplifiers to be connected to the differential amplifier means while selecting one of the buffer amplifiers formerly connected to the differential amplifier means to be connected as the ground means.

19. The invention as set forth in claim 17, wherein there are four of said sensor means, the first one of the four sensor means being adapted to be attached to the left side of the upper chest, the second one of the four sensor means being adapted to be attached to the right side of the upper chest, the third one of the four sensor means being adapted to be attached to the lower left quadrant of the abdomen, and a fourth one of the four sensor means being adapted to be attached in the region of the $V_1$ position.

20. A biological monitoring system comprising:
   sensor means for generating at least one sensor signal in response to biological action;
   conductor means for conducting the sensor signal;
   shield means for shielding said conductor means;
   signal processor means for generating an output signal in response to the conducted sensor signal;
   indicator means responsive to the output signal for providing an indication of information carried by the output signal; and
   feedback means for exciting said shield means in response to the conducted sensor signal to increase impedance of said conductor means.

21. The system as set forth in claim 20 above wherein said feedback means includes means for exciting said shield means to reduce capacitive coupling between said conducting means and said shield means.

22. The invention as set forth in claim 20, wherein the sensor means comprise electrode means for generating a plurality of sensor signals in response to cardiac action, said electrode means including at least three electrodes, and the signal processing means includes select means for generating select signals, said select means including for generating a first select signal to select a first output signal, means for generating a ground signal and means for generating a second select signal to select a second output signal, first signal processing means for generating the first output signal in response to the first select signal, said first signal processing means including means for generating the output signal in response to a difference between signals from a first pair of said electrodes in response to the first select signal and means for connecting the ground signal to a first ground electrode in response to the first select signal, and second signal processing means for generating the second output signal in response to the second select signal, said second signal processing means including means for generating the output signal in response to a difference between signals from a second pair of said electrodes in response to the second select signal and means for connecting the ground signal to a second ground electrode in response to the second select signal wherein said second ground electrode is included in said first pair of said electrodes, and further including monitoring means for monitoring an output signal in response to the select signals.

23. The invention as set forth in claim 20, wherein the sensor means comprises four electrodes, the first electrode being adapted to be attached to the left shoulder of a patient, the second electrode being adapted to be attached to the right shoulder of a patient, the third electrode being adapted to be attached to a patient in the area of the $V_5$ position, and the fourth electrode being adapted to be attached to a patient in the area of the $V_1$ position.

24. The invention as set forth in claim 20, wherein the sensor means generates a plurality of sensor signals in response to biological action and further including means responsive to the sensor signals for providing an indication of information carried thereby, means for processing said sensor signals, said means for processing having a saturated level, means for electronically switching to each of said sensor signals for a selected period of time in a given sequence in a repetitive cycle, means for generating a synchronization pulse marking the beginning of each repetitive cycle, each synchronization pulse having a predetermined magnitude related to the saturated level of said procesing means, means for settling out the transient signal variations accompanying switching in a time period which is small relative to said selected period of time for each of said sensor signals, means for transmitting said processed signals and each occurrence of the syncchronization pulse, and means responsive to the transmitted processed signals and each occurrence of the synchronization pulse for providing an indication of each occurrence of the synchronization pulse.

25. A cardiac monitoring system comprising the combination of:
   means adapted to be responsive to cardiac activity of a patient for generating a first signal having horizontal EKG cardiac signal information;
   means adapted to be responsive to cardiac activity of a patient for generating a second signal having vertical cardiac signal information;
   means adapted to be responsive to cardiac activity of a patient for generating a third signal having anterior-posterior cardiac information as well as precordial information in the vicinity of the heart apex;
   means adapted to be responsive to cardiac activity of a patient for generating a fourth signal having $V_5$ precordial information as well as transthoracic information, the fourth signal containing about 90% of the ischemic information of a conventional 12 lead EKG; and
   means responsive to the first, second, third and fourth signals for processing said signals to provide an indication of cardiac activity.

26. A method for obtaining data on the cardiac action of a patient comprising the steps of:
   coupling first electrode means to the right side of the manubrium of the patient;
   coupling second electrode means to the outer left clavicle of the patient;
   coupling third electrode means to the patient substantially at the $V_5$ position;
   coupling fourth electrode means to the patient substantially at the $V_1$ position;
   successively coupling different combinations of three of the first, second, third and fourth electrode means to provide cardiac signals, the cardiac signals comprising the difference between signals on two of the electrode means of each combination of three with the third electrode means of the combination of three being coupled as a grounded reference; and
   providing a display of cardiac information carried by the cardiac signals.

27. The invention as set forth in claim 26, wherein the step of successively coupling includes coupling the first and second electrode means to provide a cardiac signal and one of the third and fourth electrode means as a grounded reference, coupling the first and third electrode means to provide a cardiac signal and one of the second and fourth electrode means as a grounded reference, coupling the second and third electrode means to provide a cardiac signal and one of the first and fourth electrode means as a grounded reference, and coupling the second and fourth electrode means to provide a cardiac signal and one of the first and third electrode means as a grounded reference.

28. A system for processing electrical currents due to potentials accompanying cardiac action of an ambulatory patient or electrical impulses from a pulse generator designed to pace the heart for multiplex transmission to monitoring facilities, comprising: a plurality of electrodes adapted to electrically contact the body of a patient, amplifying means for amplifying signals fed thereto, means coupled to the amplifying means for providing an indication of information carried by amplified signals from the amplifying means, a plurality of buffer amplifier means coupled between the amplifying means and the electrodes, sequencing means coupled to and controlling the buffer amplifier means, the sequencing means including means for rendering selected ones of the buffer amplifier means conductive to pass signals to the amplifying means, and hole means for preventing operation of the sequencing means to continue passage of signals by the buffer amplifier means to the amplifying means in response to potentials from selected ones of the electrodes.

29. A cardiac monitoring system comprising the combination of:
   means responsive to cardiac activity of a patient for generating a first signal having horizontal EKG cardiac signal information;
   means responsive to cardiac activity of a patient for generating a second signal having vertical cardiac signal information;
   means responsive to cardiac activity of a patient for generating a third signal having anterior-posterior cardiac information and heart apex precordial information;
   means responsive to cardiac activity of a patient for generating a fourth signal having $V_5$ precordial information and transthoracic information; and
   means responsive to the first, second, third and fourth signals for processing said signals to provide an indication of cardiac activity.

* * * * *